(12) United States Patent
Policello et al.

(10) Patent No.: US 9,988,404 B2
(45) Date of Patent: Jun. 5, 2018

(54) ESTER-MODIFIED ORGANOSILICON-BASED SURFACTANTS, METHODS OF MAKING SAME AND APPLICATIONS CONTAINING THE SAME

(71) Applicant: Momentive Performance Materials Inc., Waterford, NY (US)

(72) Inventors: George A. Policello, Ossining, NY (US); Narayan Mukherjee, Sleepy Hollow, NY (US); Roland Wagner, Bonn (DE); Mark D. Leatherman, Stamford, CT (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days. days.

(21) Appl. No.: 15/092,751

(22) Filed: Apr. 7, 2016

(65) Prior Publication Data

US 2017/0291914 A1 Oct. 12, 2017

(51) Int. Cl.
| | | |
|---|---|---|
| *C07F 7/08* | (2006.01) |
| *A01N 57/20* | (2006.01) |
| *A01N 25/30* | (2006.01) |
| *A61Q 15/00* | (2006.01) |
| *A61Q 9/02* | (2006.01) |
| *A61Q 19/00* | (2006.01) |
| *A61Q 19/10* | (2006.01) |
| *A61Q 5/02* | (2006.01) |
| *A61Q 5/12* | (2006.01) |
| *A61Q 5/06* | (2006.01) |
| *A61Q 5/08* | (2006.01) |
| *A61Q 3/02* | (2006.01) |
| *A61Q 3/04* | (2006.01) |
| *A61Q 17/04* | (2006.01) |
| *A61Q 1/06* | (2006.01) |
| *A61Q 1/02* | (2006.01) |
| *A61Q 1/10* | (2006.01) |
| *A61Q 1/08* | (2006.01) |
| *A61K 8/58* | (2006.01) |
| *C11D 1/82* | (2006.01) |
| *C11D 11/00* | (2006.01) |

(52) U.S. Cl.
CPC ............ *C07F 7/0818* (2013.01); *A01N 25/30* (2013.01); *A01N 57/20* (2013.01); *A61K 8/585* (2013.01); *A61Q 1/02* (2013.01); *A61Q 1/06* (2013.01); *A61Q 1/08* (2013.01); *A61Q 1/10* (2013.01); *A61Q 3/02* (2013.01); *A61Q 3/04* (2013.01); *A61Q 5/02* (2013.01); *A61Q 5/06* (2013.01); *A61Q 5/065* (2013.01); *A61Q 5/08* (2013.01); *A61Q 5/12* (2013.01); *A61Q 9/02* (2013.01); *A61Q 15/00* (2013.01); *A61Q 17/04* (2013.01); *A61Q 19/007* (2013.01); *A61Q 19/10* (2013.01); *C07F 7/0827* (2013.01); *C11D 1/82* (2013.01); *C11D 11/0017* (2013.01); *C11D 11/0023* (2013.01); *C11D 11/0035* (2013.01)

(58) Field of Classification Search
None
See application file for complete search history.

(56) References Cited

U.S. PATENT DOCUMENTS

| | | |
|---|---|---|
| 3,159,601 A | 12/1964 | Ashby |
| 3,220,972 A | 11/1965 | Lamoreaux |
| 3,669,939 A | 6/1972 | Baker et al. |
| 3,715,334 A | 2/1973 | Karstedt |
| 3,749,753 A | 7/1973 | Gannon |
| 3,775,452 A | 11/1973 | Karstedt |
| 3,814,730 A | 6/1974 | Karstedt |
| 4,698,178 A | 10/1987 | Huttinger et al. |
| 5,104,647 A | 4/1992 | Policello |
| 5,136,063 A | 8/1992 | O'Lenick, Jr. |
| 5,180,843 A | 1/1993 | O'Lenick, Jr. |
| 5,210,133 A | 5/1993 | O'Lenick, Jr. |
| 5,226,923 A | 7/1993 | O'Lenick, Jr. |
| 5,248,783 A | 9/1993 | O'Lenick, Jr. |
| 5,411,729 A | 5/1995 | O'Lenick, Jr. |
| 5,446,183 A | 8/1995 | O'Lenick, Jr. |
| 5,446,184 A | 8/1995 | O'Lenick, Jr. |
| 5,475,125 A | 12/1995 | O'Lenick, Jr. |
| 5,558,806 A | 9/1996 | Policello et al. |
| 5,663,247 A | 9/1997 | Sorensen et al. |
| 5,674,832 A | 10/1997 | Keys |

(Continued)

FOREIGN PATENT DOCUMENTS

| | | |
|---|---|---|
| DE | 4318536 | 12/1994 |
| DE | 102008032064 | 1/2010 |

(Continued)

OTHER PUBLICATIONS

J.V. Dzunuzovic et al., Journal of Non-Crystalline Solids 358 (2012) pp. 3161-3169.A1.
S. Boye et al., Polymer 51 (2010) pp. 4110-4120.
Gaskin et al., "Antagonism of the Foliar Uptake of Glyphosate into Grasses by Organosilicone Surfactants, Part 1: Effects of Plant Species, Formulation, Concentrations and Timing of Application", Pestic Sci. 38 (1993) pp. 185-192.
J.L. Spier, "Homogeneous Catalysis of Hydrosilation by Transition Metals", Advances in Organometallic Chemistry, (1979) vol. 17, pp. 407-447.

(Continued)

*Primary Examiner* — Mina Haghighatian
*Assistant Examiner* — Luke E Karpinski
(74) *Attorney, Agent, or Firm* — Joseph S. Ostroff

(57) ABSTRACT

There is provided herein a polyalkylene-oxide-free surfactant composition comprising an ester-modified organosilicon having the general formula (I)

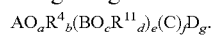

There is also provided methods for making the ester-modified organosilicon (I) and agricultural, coating, personal care and home care applications containing the polyalkylene-oxide-free surfactant composition.

29 Claims, No Drawings

(56) References Cited

U.S. PATENT DOCUMENTS

| | | |
|---|---|---|
| 6,045,156 A | 4/2000 | Perry |
| 6,054,547 A | 4/2000 | Perry et al. |
| 6,060,546 A | 5/2000 | Powell et al. |
| 6,075,111 A | 6/2000 | Perry et al. |
| 6,077,923 A | 6/2000 | Perry et al. |
| 6,083,901 A | 7/2000 | Perry et al. |
| 6,090,758 A | 7/2000 | Pillon et al. |
| 6,153,578 A | 11/2000 | Perry |
| 6,221,811 B1 | 4/2001 | Policello et al. |
| 6,271,295 B1 | 8/2001 | Powell et al. |
| 6,388,042 B1 | 5/2002 | O'Lenick, Jr. |
| 6,649,705 B2 | 11/2003 | Ramesh |
| 6,727,340 B1 | 4/2004 | O'Lenick, Jr. |
| 6,891,051 B1 | 5/2005 | Wohlman et al. |
| 7,083,800 B1 | 8/2006 | Terren et al. |
| 7,199,095 B2 | 4/2007 | Lentsch et al. |
| 7,399,734 B2 | 7/2008 | Grabowski et al. |
| 7,655,744 B2 | 2/2010 | Miyanaga |
| 2003/0096919 A1 | 5/2003 | Ichinohe |
| 2004/0009131 A1 | 1/2004 | Simonnet et al. |
| 2004/0071741 A1 | 4/2004 | Derian |
| 2005/0008592 A1 | 1/2005 | Gardel et al. |
| 2005/0084467 A1 | 4/2005 | Miyanaga |
| 2005/0261133 A1 | 11/2005 | Nakanishi et al. |
| 2006/0013793 A1 | 1/2006 | Themens |
| 2007/0269467 A1 | 11/2007 | Leatherman et al. |
| 2008/0167390 A1 | 7/2008 | Archer et al. |
| 2008/0207842 A1 | 8/2008 | Barthel et al. |
| 2010/0160577 A1* | 6/2010 | Hirano ............... C08L 83/04 525/477 |
| 2015/0056155 A1 | 2/2015 | Wagner et al. |
| 2015/0299400 A1 | 10/2015 | Wagner et al. |
| 2016/0100573 A1 | 4/2016 | Policello et al. |
| 2016/0102179 A1 | 4/2016 | Wagner et al. |

FOREIGN PATENT DOCUMENTS

| | | |
|---|---|---|
| EP | 0 091 257 A2 | 10/1983 |
| EP | 1 683 852 A1 | 7/2006 |
| EP | 1 816 154 A1 | 8/2007 |
| EP | 2 030 605 A1 | 3/2009 |
| EP | 2 223 989 A1 | 9/2010 |
| EP | 2 243799 A1 | 10/2010 |
| JP | 2005-082925 | 4/1993 |
| JP | 2005-089494 | 4/1993 |
| WO | 2007/075927 A1 | 7/2007 |
| WO | 2007/139615 | 12/2007 |
| WO | 2011/064255 A1 | 6/2011 |
| WO | 2013/148629 | 10/2013 |
| WO | 2016057288 A1 | 4/2016 |

OTHER PUBLICATIONS

Policello et al., "Influence of Trisiloxane Alkoxylate Blends on the Perofrmance of Glyphosate on Barnyardgrass", Plant Protection Chemistry NZ, Forest Research, P. Bag 3020, Rotorua, New Zealand, pp. 4810486.

B. Grüning et al., "Neuartige Emuisionen mit siliziumorganischen Copolymeren als Emulgatoren", Special Surfactants, Tenside Surf. Det. 29; pp. 78-83 (1992) 2.

D. Schaefer, "Silicone Surfactants; Part II: Organomodified Polydimethyl Siloxanes as Surface Active Ingredients in Cosmetic Formulations", Special Surfactants, Tenside Surf. Det. 27; pp. 154-158 (1990) 3.

R. Wagner et al., "Silicon-Modified Cartohydrate Surfactants II: Siloxanyl Moieties Containing Branched Structures", Applied Organometallic Chemistry, vol. 10, pp. 437-450; (1996).

H.G. Hauthal et al., "A Report of: The 53rd SEPAWA Congress with 2nd European Detergents Conference 2006", SÖFW—International Journal for Applied Sciences, vol. 132, Dec. 2006.

International Search Report and Written Opinion from PCT/US2017/024666 dated Jul. 3, 2017.

* cited by examiner

ESTER-MODIFIED ORGANOSILICON-BASED SURFACTANTS, METHODS OF MAKING SAME AND APPLICATIONS CONTAINING THE SAME

FIELD OF THE INVENTION

The present invention is directed to surfactants, more specifically, ester-modified organosilicon-based surfactants and their use in agricultural, coating, personal care and home care applications.

BACKGROUND OF THE INVENTION

Surfactants have been used widely in many fields. In the use of surfactants, properties such as wetting, spreading, foaming, detergency, and the like are important in the various applications in which they are employed.

Additionally, some surfactants have been shown to inhibit the uptake of various agrochemicals in various plant species. Thus, it would be advantageous to provide a surfactant that maintains desirable surfactant properties while also providing for increased uptake of agrochemicals in various plant species.

BRIEF DESCRIPTION OF THE INVENTION

In accordance with the present invention, there has been unexpectedly discovered herein that the use of various nonionic, ester-modified organosilicon surfactants, wherein the hydrophilic moiety is substantially free of polyalkylene oxide moieties, provides for enhanced uptake of chemicals in various applications, such as the improved uptake of agrochemicals in various plant species. More specifically, it has been discovered herein that the ester-modified organosilicon surfactants described herein have improved uptake of glyphosate into grasses over that of polyalkyleneoxide modified carbosilane surfactants.

In accordance with the invention there is provided herein, a polyalkylene-oxide-free surfactant composition comprising an ester-modified organosilicon having the general formula (I):

$$AO_aR^4{}_b(BO_cR^{11}{}_d)_e(C)_fD_g \quad (I)$$

wherein the ester-modified organosilicon contains from 1 to 3 silicon atoms, and optionally at least one heteroatom, and a hydrophilic or lipophilic ester or polyester group derived from hydroxyl carboxylic acids, and wherein the ester-modified organosilicon is substantially free of polyalkylene oxide moieties such as polyethylene oxide moieties, polypropylene oxide moieties and polybutylene oxide moieties, where
$A=R^1R^2R^3Si—$
$B=—Si(R^5)(R^6)—$
$C=R^7R^8R^9Si—$
$D=—O(R^{14})_pR^{19}$ where $R^4$ and $R^{11}$ are independently selected from a branched or linear divalent hydrocarbon radical of 1 to 12 carbons, more specifically 2 to 4 of carbons atoms, subscripts a, b, c, d, e, f, g and p are each 0 or 1 and subject to the following provisos:

a+b=1; when e=1, c+d=1; and, when g=1, then a+e+f=0;
$R^1R^2R^3R^5R^7R^8$ are each independently selected from the group consisting of monovalent hydrocarbon radicals having from 1 to 8 carbon atoms, more specifically from 1 to 6 carbons, and an aryl or alkaryl hydrocarbon radical of from 6 to 12 carbon atoms, or $R^{10}$;

where each $R^{10}$ is independently selected from the group consisting of branched monovalent hydrocarbon radicals of from 3 to 6 carbon atoms, such as the non-limiting examples of isopropyl, t-butyl and t-amyl;

$R^6$ and $R^9$ are each independently selected from the group consisting of linear or branched monovalent hydrocarbon radicals containing from 1 to 8 carbon atoms, more specifically containing from 1 to 4 carbon atoms, or $R^{12}$, provided that in formula (I) $R^6$ and $R^9$ are different and one of $R^6$ and $R^9$ is $R^{12}$, wherein $R^{12}$ is $—R^{13}O(R^{14})_pR^{19}$ or a cyclohexyl group of the general formula (Q):

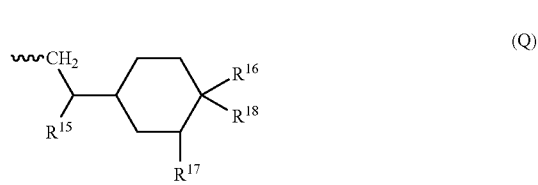

(Q)

where $R^{13}$ is selected from a branched or linear divalent hydrocarbon radical containing from 3 to 12 carbon atoms, more specifically from 3 to 6 carbon atoms, which is optionally —OH substituted;

$R^{14}$ is selected from $—CH_2CH(R^{20})CH_2O—$, $—CH_2(CH_2)_xCH(R^{20})CH_2O—$, or a bridging group of the general formula (Y):

$$—[C_2H_4O]_h—[C_3H_6O]_i—[C_4H_8O]_j—[C_2H_4O]_k—[CH_2CH(R^{20})CH_2O]_n— \quad (Y);$$

wherein subscripts h, i, j, and k are zero or one and satisfy the following relationships:
0≤h+i+j≤1, and 0≤h+k≤1
$R^{20}$ is H, OH or $—OR^{19}$,
subscript x is from 1 to 9,
subscripts p and n are 0 or 1, and
$R^{15}$ and $R^{16}$ are each independently selected from H or methyl;
$R^{17}$ and $R^{18}$ are each independently OH or $—OR^{19}$; provided that in formula (Q) $R^{17}$ and $R^{18}$ are the same or different, and at least one of $R^{17}$ and $R^{18}$ is $OR^{19}$, where $R^{19}$ is derived from the esterification of the corresponding hydroxy carboxylic acid or a mixture of corresponding hydroxy carboxylic acids, which hydroxy carboxylic acid(s) contain(s) from 2 to 8 carbon atoms, more specifically from 2 to 5 carbon atoms and where $R^{19}$ is of the general formula (Z):

$$—C(=O)—CR^{21}R^{22}R^{23} \quad (Z)$$

where $R^{21}$, $R^{22}$, $R^{23}$ are each independently selected from H, —OH, $—CH_2OH$, $—OZ$, $—(R^{24})_mO—R^{27}$, $—CH_3$, $—CH_2CH_3$, or $—(R^{24})_mO—C(=O)$ $(CR^{25}R^{26})_tCH_2OR^{27}$ where $R^{24}$ is a divalent hydrocarbon radical of 1 to 3 carbon atoms, $R^{25}$ and $R^{26}$ are each independently selected from H, —OH, $—CH_2OH$, $—OZ$, $—(R^{24})_mO—R^{27}$, $—CH_3$, $—CH_2CH_3$, or $—(R^{24})_mO—C(=O)—(CR^{25}R^{26})_tCH_2OR^{27}$ $R^{27}$ is independently selected from H, Z, $—CH_2OH$, $—CH_3$, $—CH_2CH_3$, or $[—C(=O)(CR^{25}R^{26})_tCH_2O]_w—R^{29}$, $R^{29}$ is independently selected from H, $—CH_2OH$, $—CH_3$, or $—CH_2CH_3$ subscript m is 0 to 3, t is 1 to 5 and w is 1 to 5; provided that the number of Z groups in $R^{19}$ is between 1 and 10, more specifically between 2 and 10; and, provided that when any one or more of $R^{21}$, $R^{22}$ and $R^{23}$ are of the formula —$(R^{24})_mO$—$C(=O)$—$(CR^{25}CR^{26})_tCH_2OR^{27}$ that $R^{21}$, $R^{22}$ or $R^{23}$ group has from 1 to 10 —$(R^{24})_mO$—$C(=O)$—$(CR^{25}CR^{26})_tCH_2OR^{27}$ groups, more specifically from 2 to 10 —$(R^{24})_mO$—$C(=O)$—$(CR^{25}CR^{26})_tCH_2OR^{27}$ groups.

The expression "polyalkylene-oxide-free" is understood to mean that the ester-modified organosilicon having the general formula (I) herein, and optionally, compositions containing the ester-modified organosilicon as described herein is substantially or completely absent of polyalkylene oxide moieties such as the non-limiting examples of polyethylene oxide moieties, polypropylene oxide moieties, polybutylene oxide moieties and the like, most specifically wherein in the ester-modified organosilicon having the general formula (I) herein, the hydrophilic moiety is substantially or completely absent such polyalkylene oxide moieties.

In one embodiment the expression "substantially absent" as pertains to the polyalkylene oxide moieties of the ester-modified organosilicon having the general formula (I) herein is understood to be less than 5 mole percent, preferably less than 1 mole percent, and more preferably less than 0.1 mole percent based on the mole content of the ester-modified organosilicon having the general formula (I), whether it is present in a composition containing the same as described herein, or not. Further such ranges of mole percent can in one non-limiting embodiment have a lower endpoint of 0.001 mole percent.

Various other features, aspects and advantages of the present invention, will become more apparent with reference to the following description and appended claims.

DETAILED DESCRIPTION OF THE INVENTION

In one embodiment herein the ester-modified organosilicon has the general formula (I), which is described above, wherein $R^{19}$ is selected from the groups consisting of alpha-hydroxy acids, beta-hydroxy acids and dihydroxy acids, where the number of ester groups in $R^{19}$ are between 1 and 10.

In a more specific embodiment herein, the ester-modified organosilicon has the general formula (II):

$$AOC \quad\quad\quad (II)$$

wherein:
A=$R^1R^2R^3Si$—
C=$R^7R^8R^9Si$—
wherein each of $R^2$, $R^3$, $R^7$ and $R^8$ are methyl,
$R^1$ is a neo-hexyl group,
$R^9$ is $R^{12}$, where $R^{12}$ is —$R^{13}O(R^{14})_pR^9$
where —$R^{13}$ is a divalent hydrocarbon radical having 3 carbon atoms,
$R^{14}$ is —$CH_2CH(R^{20})CH_2O$—
$R^{20}$ is OH
$R^{19}$ is —$C(=O)$—$CR^{21}R^{22}R^{23}$ formula (Z),
where $R^{22}$ is methyl
$R^{21}$ and $R^{23}$ are —$(R^{24})_mO$—$R^{27}$,
where $R^{24}$ is a divalent hydrocarbon of 1 to 3 carbon atoms,
$R^{27}$ is Z or H, providing
that the number of Z units in $R^{19}$ is about 3 to 4,
subscripts m and p are 1; and,
the hydroxy acid is selected from dimethylol propionic acid, glycolic acid, gluconic acid and lactic acid.

In another specific embodiment herein, the ester-modified organosilicon of the present invention has the general formula (III):

$$AR^4C \quad\quad\quad (III)$$

wherein
A=$R^1R^2R^3Si$—
C=$R^7R^8R^9Si$—
where $R^1$, $R^2$, $R^3$, $R^7$ and $R^8$ are methyl,
$R^4$ is —$CH_2CH_2$—
$R^9$ is $R^{12}$, where $R^{12}$ is —$R^{13}O(R^{14})_pR^{19}$
where —$R^{13}$ is a divalent hydrocarbon radical having 3 carbon atoms
$R^{14}$ is —$CH_2CH(R^{20})CH_2O$—
$R^{20}$ is OH
$R^{19}$ is —$C(=O)$—$CR^{21}R^{22}R^{23}$ formula (Z),
where $R^{22}$ is methyl
$R^{21}$ and $R^{23}$ are —$(R^{24})_mO$—$R^{27}$
where $R^{24}$ is a divalent hydrocarbon of 1 to 3 carbon atoms,
$R^{27}$ is Z or H, providing that the number of Z units in $R^{19}$ is about 3 to 4;
subscripts m and p are 1; and,
the hydroxy acid is selected from dimethylol propionic acid, glycolic acid, gluconic acid and lactic acid.

In yet another specific embodiment the ester-modified organosilicon has the general formula (IV):

$$AR^4BOC \quad\quad\quad (IV)$$

wherein
A=$R^1R^2R^3Si$—
B=—$Si(R^5)(R^6)$—
C=$R^7R^8R^9Si$—
$R^1$, $R^2$, $R^3$, $R^7$ and $R^8$ are methyl,
$R^4$ is —$CH_2CH_2$—
$R^9$ is $R^{12}$, where $R^{12}$ is —$R^{13}O(R^{14})_pR^{19}$
where —$R^{13}$ is a divalent hydrocarbon radical having 3 carbon atoms,
$R^{14}$ is —$CH_2CH(R^{20})CH_2O$—
$R^{20}$ is OH
$R^{19}$ is —$C(=O)$—$CR^{21}R^{22}R^{23}$ formula (Z),
where $R^{22}$ is methyl
$R^{21}$ and $R^{23}$ are —$(R^{24})_mO$—$R^{27}$,
where $R^{24}$ is a divalent hydrocarbon of 1 to 3 carbon atoms,
$R^{27}$ is Z or H, providing that the number of Z units in $R^{19}$ is about 4 to 6,
subscripts m and p are 1; and,
the hydroxy acid is selected from dimethylol propionic acid, glycolic acid, gluconic acid and lactic acid.

Another specific embodiment the ester-modified organosilicon has the general formula (V):

$$AR^4C \quad\quad\quad (V)$$

wherein
A=$R^1R^2R^3Si$—
C=$R^7R^8R^9Si$—
$R^1$, $R^2$, $R^3$, $R^7$ and $R^8$ are methyl,
$R^4$ is —$CH_2CH_2$—
$R^9$ is $R^{12}$, where $R^{12}$ is —$R^{13}O(R^{14})_pR^{19}$
where —$R^{13}$ is a divalent hydrocarbon radical having 3 carbon atoms
$R^{19}$ is —$C(=O)$—$CR^{21}R^{22}R^{23}$ formula (Z),
wherein $R^{21}$ and $R^{23}$ are H,
$R^{22}$ is $(R^{24})_mO$—$R^{27}$,
where $R^{24}$ is a divalent hydrocarbon of 1 to 3 carbon atoms, $R^{27}$ is Z or H providing that the number of Z units in $R^{19}$ is about 4 to 5, subscript m is 1, and subscript p is 0; and, the hydroxy acid is selected from dimethylol propionic acid, glycolic acid, gluconic acid and lactic acid.

Still another specific embodiment the ester-modified organosilicon has the general formula (VI):

$$AOBOC \qquad (VI)$$

wherein, $A=R^1R^2R^3Si—$ $B=—Si(R^5)(R^6)—$ $C=R^7R^8R^9Si—$ $R^1$, $R^2$, $R^3$, $R^7$, $R^8$ and $R^9$ are methyl, $R^6$ is $R^{12}$, where $R^{12}$ is $—R^{13}O(R^{14})_pR^{19}$ where $—R^{13}$ is a divalent hydrocarbon radical having 3 carbon atoms $R^{14}$ is $—CH_2CH(R^{20})CH_2O—$ $R^{20}$ is OH $R^{19}$ is $—C(=O)—CR^{21}R^{22}R^{23}$ formula (Z), where $R^{22}$ is methyl $R^{21}$ and $R^{23}$ are $—(R^{24})_mO—R^{27}$, where $R^{24}$ is a divalent hydrocarbon of 1 to 3 carbon atoms, $R^{27}$ is Z or H providing that the number of Z units in $R^{19}$ is about 4 to 6, subscripts m and p are each 1; and, the hydroxy acid is selected from dimethylol propionic acid, glycolic acid, gluconic acid and lactic acid.

Still another specific embodiment the ester-modified organosilicon has the general formula (VII):

$$AR^4D \qquad (VII)$$

wherein $A=R^1R^2R^3Si—$ $R^4$ is a divalent hydrocarbon radical of 6 carbon atoms;

$D=—O(R^{14})\ R^{19}$ where $R^1R^2$ and $R^3$ are each methyl;

$R^{14}$ is $—CH_2CH(R^{20})CH_2O—$ where $R^{20}$ is OH;

$R^{19}$ is $—C(=O)—CR^{21}R^{22}R^{23}$ formula (Z), where $R^{22}$ is methyl;

$R^{21}$ and $R^{23}$ are $—(R^{24})_mO—R^{27}$, where $R^{24}$ is a divalent hydrocarbon of 1 to 3 carbon atoms, $R^{27}$ is Z or H, providing that the number of Z units in $R^{19}$ is about 3 to 6, the subscripts m and p are each 1; and, the hydroxy acid is selected from dimethylol propionic acid, glycolic acid, gluconic acid and lactic acid.

Another specific embodiment the ester-modified organosilicon has the general formula (VIII):

$$AR^4C \qquad (VIII)$$

wherein $A=R^1R^2R^3Si—$ $C=R^7R^8R^9Si—$ $R^1$, $R^2$, $R^3$, $R^7$ and $R^8$ are methyl, $R^4$ is $—CH_2CH_2—$ $R^9$ is $R^{12}$ of the formula (Q)

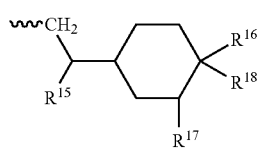

(Q)

where $R^{15}$ and $R^{16}$ are methyl $R^{17}$ and $R^{18}$ are $—OH$ or $—OR^9$; provided that in (Q) $R^{17}$ and $R^{18}$ are the same or different, and at least one of these substituents is $OR^{19}$.

$R^{19}$ is $—C(=O)—CR^{21}R^{22}R^{23}$ formula (Z), wherein $R^{21}$ and $R^{23}$ are H, $R^{22}$ is $—(R^{24})_mO—C(=O)\ (CR^{25}R^{26})_tCH_2OR^{27}$ where $R^{24}$ is a divalent hydrocarbon of 1 to 3 carbon atoms, $R^{25}$ and $R^{26}$ are H, $—OH$, $—(R^{24})_mO—C(=O)—(CR^{25}R^{26})_tCH_2OR^{27}$, where $R^{27}$ is H, or $[—C(=O)(CR^{25}R^{26})_tCH_2O]_w—R^{29}$, $R^{29}$ is H, providing that the number of Z units in $R^{19}$ is about 3 to 4;

t is 4 or 5, m is 1, 1 and w is 2 to 3, provided that $R^{22}$ has from 1 to 10 $—(R^{24})mO—C(=O)—(CR^{25}CR^{26})_tCH_2OR^{27}$ groups.

The hydroxy carboxylic acids, such as those described in the formation of $R^{19}$ in formula (Z) above, inter alia, and those that are described herein in the various embodiments herein can be used interchangeably in any of the embodiments herein. In one specific embodiment the hydroxyl carboxylic acid is selected from the group consisting of, but not limited to, alpha-hydroxy acids (such as glycolic acid, lactic acid, citric acid, tartaric acid and mandelic acid), beta-hydroxy acids (such as hydroxy propionic acids, salicylic acid, carnitine, β-Hydroxy β-methylbutyric acid and 3-hydroxybutyric acid), dihydroxy acids (e.g. dimethylol propionic acid, dimethylol butanoic acid, dihydroxymandelic acid, and dihydroxybenzoic acids), and polyhydroxy acids, such as gluconic acid, glucoronic acid, and their oligomeric or polymeric condensation products.

There is also provided herein a method of making the ester-modified organosilicon having the general formula (I), and/or any of the formulae (II)-(VIII) described herein, which method comprises:

(a) reacting a corresponding hydride intermediate with an olefinically-modified intermediate in the presence of a catalyst, such as a silylation catalyst, such as the non-limiting examples of precious metal catalysts such as those described herein; and where, in one embodiment, the corresponding hydride intermediate is selected from the group of consisting of formulae (I-a):

$$AO_aR^4{}_b(B^HO_cR^{11}{}_d)_eC^H \qquad (I-a)$$

wherein:

$A=R^1R^2R^3Si—$;

$B^H=—Si(R^5)(R^{6H})—$;

$C^H=R^7R^8R^{9H}Si—$;

subscripts a, b, c, d and e are 0 or 1 and subject to the following relationships:

a+b=1 and when e=1, c+d=1;

$R^1$, $R^2$, $R^3$, $R^5$, $R^7$, $R^8$ are independently selected from the group consisting of monovalent hydrocarbon groups containing from 1 to 8 carbon atoms, more specifically from 1 to 4 carbon atoms, and monovalent aryl and alkaryl hydrocarbon groups containing from 6 to 12 carbon atoms, or $R^{10}$, wherein $R^{10}$ is selected from a group consisting of branched monovalent hydrocarbon groups of containing from 3 to 6 carbon atoms, such as the non-limiting examples of isopropyl, t-butyl and t-amyl;

$R^4$ and $R^{11}$ are independently selected from the group consisting of a divalent hydrocarbon group containing from 1 to 4 carbon atoms, more specifically from 1 to 3 carbon atoms;

$R^{6H}$ and $R^{9H}$ are selected from the group consisting of linear or branched monovalent hydrocarbon groups containing from 1 to 8 carbon atoms, more specifically from 1 to 4 carbon atoms, or hydrogen, provided that in (I-a) $R^{6H}$ and $R^{9H}$ are different and at least one $R^{6H}$ or $R^{9H}$ is hydrogen, and In one embodiment herein Q is the reaction product of the organosilicon hydride and vinylcyclohexene oxide.

and wherein an olefinically-modified intermediate is a molecule containing one or more oxirane or oxetane groups and containing one or more, terminal or pendant carbon-carbon double bonds, and contains from 4 to 12 carbon atoms, such as the non-limiting examples of allyl oxiranes such as olefinically modified epoxides, such as those of the general formula:

$CH_2$=CH—$(CH_2)_y$O$CH_2$CH(O)$CH_2$, where subscript y is 3 to 12, or

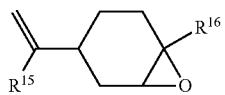 (IX)

where $R^{15}$ and $R^{16}$ are as described above, and where one non-limiting example of olefinically-modified intermediate is cyclohexeneoxide;

to produce an epoxy-modified organosilicon intermediate; and, (b) adding the epoxy-modified organosilicon intermediate to a carboxylic acid-terminated oligomer in the presence of a catalyst, such as the non-limiting example of a tertiary amine catalyst, such as the non-limiting examples of triethyl amine, tributyl amine, pentamethyldiethylenetriamine, methyl diethanolamine, dimethyl benzylamine, triphenylamine, tricyclohexyl amine, pyridine, quinoline, dimethylaniline, diazabicyclo[2.2.2]octane, N-methylimidazole, diazabicyclo[5,4,0]undec-7-ene, 1,8-diazabicyclo[5.4.0]undec-7-en(1,5-5) and mixtures thereof; and, wherein the carboxylic acid-terminated oligomer is made by esterifying the carboxylic acid group of a hydroxy carboxylic acid with the hydroxy group of the same or a different hydroxy carboxylic acid, wherein the hydroxy carboxylic acid(s) contain from 2 to 8 carbon atoms, more specifically from 2 to 5 carbon atoms, to produce the ester-modified organosilicon having the general formula (I).

In one embodiment herein esterification of the carboxylic acid group of a hydroxy carboxylic acid with the hydroxy group of the same or a different hydroxy carboxylic acid can be conducted at any desired reaction conditions depending on the desired degree of esterification in the ester-modified organosilicon having the general formula (I) as described herein, and the esterification may be conducted in the presence of a strong acid such as the non-limiting example of sulfuric acid, and further suitable reaction conditions will not be elaborated upon in that one skilled in the art will vary those accordingly to produce the desired level of esterification, except to state that the esterification conditions described herein can be applied to any esterification described herein.

In one embodiment herein, precious metal catalysts can be used in any reaction herein describing the use of a catalyst, and specifically precious metal catalysts can be suitable for making epoxy-substituted organosilicons are also well known in the art and comprise complexes of rhodium, ruthenium, palladium, osmium, iridium, or platinum. Many types of platinum catalysts for Si—H olefin addition reactions are known, and such platinum catalysts may be used to generate any of the compositions described herein. The platinum compound can be selected from those having the formula (PtCl$_2$Olefin) and H(PtCl$_3$Olefin). A further platinum containing material can be a complex of chloroplatinic acid with up to 2 moles per gram of platinum of a member selected from the class consisting of alcohols, ethers, aldehydes and mixtures thereof. Those skilled in the art can easily determine an effective amount of platinum catalyst. Generally an effective amount ranges from about 0.1 to 50 parts per million of the total epoxy modified organosilicon intermediate composition.

Another method of making the ester-modified organosilicon having the general formula (I), and/or any of the formulae (II)-(VIII) described herein, comprises reacting a corresponding hydride intermediate of the general formula (I-a):

$$AO_aR^4{}_b(B^HO_cR^{11}{}_d)_eC^H \qquad (\text{I-a})$$

wherein:
A=$R^1R^2R^3$Si—;
$B^H$=—Si($R^5$)($R^{6H}$)—;
$C^H$=$R^7R^8R^{9H}$Si—;

subscripts a, b, c, d and e are 0 or 1 and subject to the following relationships:
a+b=1 and when e=1, c+d=1;

$R^1, R^2, R^3, R^5, R^7, R^8$ are independently selected from the group consisting of monovalent hydrocarbon groups containing from 1 to 8 carbon atoms, more specifically from 1 to 4 carbon atoms, and monovalent aryl and alkaryl hydrocarbon groups containing from 6 to 12 carbon atoms, or $R^{10}$, wherein $R^{10}$ is selected from a group consisting of branched monovalent hydrocarbon groups of containing from 3 to 6 carbon atoms, such as the non-limiting examples of isopropyl, t-butyl and t-amyl;

$R^4$ and $R^{11}$ are independently selected from the group consisting of a divalent hydrocarbon group containing from 1 to 4 carbon atoms, more specifically from 1 to 3 carbon atoms;

$R^{6H}$ and $R^{9H}$ are selected from the group consisting of linear or branched monovalent hydrocarbon groups containing from 1 to 8 carbon atoms, more specifically from 1 to 4 carbon atoms, or hydrogen, provided that in (I-a) $R^{6H}$ and $R^{9H}$ are different and at least one $R^{6H}$ or $R^{9H}$ is hydrogen, with an olefinically-modified intermediate, as described herein, wherein the olefinically-modified intermediate possesses one or more oxirane or oxetane groups and contains one or more terminal or pendant carbon-carbon double bonds and contains from 4-12 carbon atoms, in the presence of a catalyst, such as the precious metal catalysts described herein, to produce an epoxy-modified organosilicon intermediate; and, reacting one equivalent of the epoxy-modified organosilicon intermediate with one equivalent of hydroxyl carboxylic acid wherein the hydroxy carboxylic acid(s) contain from 2 to 8 carbon atoms, in the presence of a catalyst, such as the catalysts described herein, to produce the ester-modified organosilicon having the general formula (I). In a further embodiment of this method, the ester-modified organosilicon having the general formula (I), is such that it contains pendant hydroxyl groups and wherein the method further optionally comprises esterifying the pendant hydroxyl groups with further carboxylic acid, such as those carboxylic acids described herein, in the presence of catalyst, such as the catalysts described herein, and then neutralizing the reaction product with an organic base.

Yet another method of making the ester-modified organosilicon having the general formula (I), and/or any of the formulae (II)-(VIII) described herein, comprises esterifying the carboxylic acid group of a hydroxy carboxylic acid with the hydroxy group of the same or a different hydroxy carboxylic acid, wherein the hydroxy carboxylic acid(s) contain from 2 to 8 carbon atoms to produce a carboxylic acid-terminated oligomer, specifically of a desired oligomerization, and, reacting the carboxylic acid-terminated oligomer with a hydroxy-modified organosilicon intermediate to produce the ester-modified organosilicon of formula (I), wherein the hydroxy-modified organosilicon intermediate is produced by reacting free carboxylic acid oligomer with an epoxy-modified organosilicon intermediate, wherein the epoxy-modified organosilicon intermediate is made by hydrosilylating olefinically modified intermediate, such as that described herein, and specifically one possessing one or more oxirane or oxetane groups and containing one or more terminal or pendant carbon-carbon double bonds and containing from 4 to 12 carbon atoms prior to hydrosilyation, optionally in the presence of a precious metal catalyst, as described herein, with a hydride intermediate which is of the formula (I-A):

$$AO_aR^4{}_b(B^HO_cR^{11}{}_d)_eC^H \qquad\qquad\text{(I-a)}$$

wherein:
$A=R^1R^2R^3Si-$;
$B^H=-Si(R^5)(R^{6H})-$;
$C^H=R^7R^8R^{9H}Si-$;

subscripts a, b, c, d and e are 0 or 1 and subject to the following relationships:
a+b=1 and when e=1, c+d=1;
$R^1, R^2, R^3, R^5, R^7, R^8$ are independently selected from the group consisting of monovalent hydrocarbon groups containing from 1 to 8 carbon atoms, more specifically from 1 to 4 carbon atoms, and monovalent aryl and alkaryl hydrocarbon groups containing from 6 to 12 carbon atoms, or $R^{10}$, wherein $R^{10}$ is selected from a group consisting of branched monovalent hydrocarbon groups of containing from 3 to 6 carbon atoms, such as the non-limiting examples of isopropyl, t-butyl and t-amyl;

$R^4$ and $R^{11}$ are independently selected from the group consisting of a divalent hydrocarbon group containing from 1 to 4 carbon atoms, more specifically from 1 to 3 carbon atoms;

$R^{6H}$ and $R^{9H}$ are selected from the group consisting of linear or branched monovalent hydrocarbon groups containing from 1 to 8 carbon atoms, more specifically from 1 to 4 carbon atoms, or hydrogen, provided that in (I-a) $R^{6H}$ and $R^{9H}$ are different and at least one $R^{6H}$ or $R^{9H}$ is hydrogen.

It will be understood herein that the expression "hydroxyl-modified organosilicon intermediate" can be used interchangeably herein with the expression "ester-modified organosilicon having the general formula (I), or any of (II)-(VIII) containing pendant hydroxyl groups".

Another method of making the ester-modified organosilicon having the general formula (I), and/or any of the formulae (II)-(VIII) described herein comprises reacting one equivalent of hydroxy carboxylic acid with one equivalent of hydroxy-modified organosilicon intermediate in the presence of catalyst, such as the non-limiting example of the tertiary amine catalysts described herein, wherein the hydroxy-modified organosilicon intermediate is produced by reacting free carboxylic acid oligomer with an epoxy-modified organosilicon intermediate wherein the epoxy-modified organosilicon intermediate is made by hydrosilylating olefinically modified intermediate possessing one or more oxirane or oxetane groups and containing one or more terminal or pendant carbon-carbon double bonds and containing from 4 to 12 carbon atoms, such as those described herein, prior to hydrosilyation with a hydride intermediate in the presence of a catalyst such as a precious metal catalyst such as those described herein, wherein the hydride intermediate is selected from the group of consisting of formulae (I-a)-(IV-a) and (VI-a)-(VII-a):

$$AO_aR^4{}_b(B^HO_cR^{11}{}_d)_eC^H \qquad\qquad\text{(I-a)}$$

$$AOC^H \qquad\qquad\text{(II-a)}$$

$$AR^4C^H \qquad\qquad\text{(III-a)}$$

$$AR^4B^HOC^H \qquad\qquad\text{(IV-a)}$$

$$AOB^HOC^H \qquad\qquad\text{(VI-a)}$$

$$AR^4D^H \qquad\qquad\text{(VII-a)}$$

wherein:
$A=R^1R^2R^3Si-$;
$B^H=-Si(R^5)(R^{6H})-$;
$C^H=R^7R^8R^{9H}Si-$; and,
$D^H=AR^{4H}$ subscripts a, b, c, d and e are each 0 or 1 and subject to the following provisos: a+b=1 and when e=1, c+d=1;

$R^1, R^2, R^3, R^5, R^7, R^8$ are independently selected from the group consisting of monovalent hydrocarbon groups containing from 1 to 8 carbon atoms, and monovalent aryl and alkaryl hydrocarbon groups containing from 6 to 12 carbon atoms, or $R^{10}$, wherein $R^{10}$ is selected from a group consisting of branched monovalent hydrocarbon groups of containing from 3 to 6 carbon atoms;

$R^4$ and $R^{11}$ are each independently selected from the group consisting of a divalent hydrocarbon group containing from 1 to 4 carbon atoms;

$R^{4H}$ is a linear or branched monovalent hydrocarbon radical of 1 to 12 carbon atoms;

$R^{6H}$ and $R^{9H}$ are independently selected from the group consisting of linear or branched monovalent hydrocarbon groups containing from 1 to 8 carbon atoms, or hydrogen,
provided that in general formulae (I-a), (IV-a) and (VI-a), $R^{6H}$ and $R^{9H}$ are different and at least one $R^{6H}$ or $R^{9H}$ is hydrogen, to produce the ester-modified organosilicon having the general formula (I), and wherein the method further optionally comprises esterifying the pendant hydroxyl groups with further carboxylic acid, such as those carboxylic acids described herein, in the presence of catalyst, such as the catalysts described herein, and then neutralizing the reaction product with an organic base.

In yet another method of making the ester-modified organosilicon having the general formula (I), and/or any of the formulae (II)-(VIII) described herein comprises:

esterifying the carboxylic acid group of a hydroxy carboxylic acid with the hydroxy group of the same or a different hydroxy carboxylic acid, as described herein for esterifying, wherein the hydroxy carboxylic acid(s) contain from 2 to 8 carbon atoms to produce a carboxylic-acid terminated oligomer;

reacting the carboxylic-acid terminated oligomer with an olefinically-modified intermediate possessing one or more oxirane or oxetane groups and containing one or more terminal or pendant carbon-carbon double bonds and containing from 4 to 12 carbon atoms in the presence of catalyst, such as the tertiary amine catalysts described herein, to obtain olefinic functionalized oligomeric ester; and, hydrosilylating the olefinic-functionalized oligomeric ester with a hydride intermediate, in the presence of a precious metal catalyst, such as those described herein wherein the hydride intermediate is selected from the group of consisting of formulae (I-a)-(IV-a) and (VI-a)-(VII-a) as described herein to make the ester-modified organosilicon having the general formula (I) described herein.

Some applications in which the ester-modified organosilicon surfactant composition can be employed are agricultural applications, coating applications, personal care applications and home care applications, as well as textiles, laundry and oil and gas applications. In general the amount of the respective ester-modified organosilicon having the general formula (I) that is used in each application will vary upon the desired application and properties thereof and can be adjusted as necessary by those skilled in the art.

The compositions of the present invention may be utilized in a variety of forms: as liquid solutions, dispersions of solids in liquids, dispersions of liquids in liquids as the previously described emulsions, solid mixtures or solid solutions either separately or in the forms previously listed in combination one with the other.\

An agricultural composition and/or a pesticide composition can be defined as any composition related to the use of fertilizers, insecticide, herbicide, fungicide, and plant growth regulators in crop, forestry, turf and ornamental, and rights-of-way applications.

The various uses/applications in which the ester-modified organosilicon surfactant composition of the present invention can be employed are as follow:

A. Pesticide Agriculture, Horticulture, Turf, Ornamental and Forestry:

Many pesticide applications require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, enhance spreading to improve spray coverage, or to provide penetration of the herbicide into the plant cuticle. These adjuvants are provided either as a tank-side additive or used as a component in pesticide formulations.

Typical uses for pesticides include agricultural, horticultural, turf, ornamental, home and garden, veterinary and forestry applications. The pesticidal compositions of the present invention also include at least one pesticide, where the ester modified organosilicon based surfactant of the present invention is present at an amount sufficient to deliver between 0.005% and 2% to the final use concentration, either as a concentrate or diluted in a tank mix. Optionally the pesticidal composition may include excipients, cosurfactants, solvents, foam control agents, deposition aids, drift retardants, biologicals, micronutrients, fertilizers and the like. The term pesticide means any compound used to destroy pests, e.g., rodenticides, insecticides, miticides, fungicides, and herbicides. Illustrative examples of pesticides that can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed.

More specific examples of pesticide compounds that can be used with the compositions of the invention are, but not limited to, herbicides and growth regulators, such as: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds. Additionally, dicamba and tembotrione.

Fungicide compositions that can be used with the present invention include, but are not limited to, aldimorph, tridemorph, dodemorph, dimethomorph; flusilazol, azaconazole, cyproconazole, epoxiconazole, furconazole, propiconazole, tebuconazole and the like; imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, maneb, mancozeb, dodicin, dodine, and metalaxyl.

Insecticides, including larvacide, miticide and ovacide compounds that can be used with the composition of the present invention, but not limited to, *Bacillus thuringiensis*, spinosad, abamectin, doramectin, lepimectin, pyrethrins, carbaryl, primicarb, aldicarb, methomyl, amitraz, boric acid, chlordimeform, novaluron, bistrifluron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrin and the like.

Fertilizers and Micronutrients:

Fertilizers or micronutrients include, but not limited to, zinc sulfate, ferrous sulfate, ammonium sulfate, urea, urea ammonium nitrogen, ammonium thiosulfate, potassium sulfate, monoammonium phosphate, urea phosphate, calcium nitrate, boric acid, potassium and sodium salts of boric acid, phosphoric acid, magnesium hydroxide, manganese carbonate, calcium polysulfide, copper sulfate, manganese sulfate, iron sulfate, calcium sulfate, sodium molybdate, calcium chloride.

The pesticide or fertilizer may be a liquid or a solid. If a solid, it is preferable that it is soluble in a solvent, or the organomodified ester modified organosilicon based surfactants of the present invention, prior to application, and the silicone may act as a solvent, or surfactant for such solubility or additional surfactants may perform this function.

Agricultural Excipients:

Buffers, preservatives and other standard excipients known in the art also may be included in the composition.

Solvents may also be included in compositions of the present invention. These solvents are in a liquid state at room temperature. Examples include water, alcohols, aromatic solvents, oils (i.e. mineral oil, vegetable oil, silicone oil, and so forth), lower alkyl esters of vegetable oils, fatty acids, ketones, glycols, polyethylene glycols, diols, paraffinics, and so forth. Particular solvents would be 2, 2, 4 trimethyl, 1 3 pentane diol and alkoxylated (especially ethoxylated) versions thereof as illustrated in U.S. Pat. No. 5,674,832 herein incorporated by reference, or n-methyl-pyrrilidone.

Cosurfactants:

Cosurfactants useful herein include nonionic, cationic, anionic, amphoteric, zwitterionic, polymeric surfactants, or any mixture thereof. Surfactants are typically hydrocarbon based, silicone based or fluorocarbon based.

Moreover, other cosurfactants, that have short chain hydrophobes that do not interfere with superspreading as described in U.S. Pat. No. 5,558,806 herein incorporated by reference are also useful.

Useful surfactants include alkoxylates, especially ethoxylates, containing block copolymers including copolymers of ethylene oxide, propylene oxide, butylene oxide, and mixtures thereof; alkylarylalkoxylates, especially ethoxylates or propoxylates and their derivatives including alkyl phenol ethoxylate; arylarylalkoxylates, especially ethoxylates or propoxylates. and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines; and so forth.

Specific examples include alkyl acetylenic diols (SURFONYL—Air Products), pyrrilodone based surfactants (e.g., SURFADONE—LP 100—Ashland), 2-ethyl hexyl sulfate, isodecyl alcohol ethoxylates (e.g., RHODASURF DA 530—Rhodia), ethylene diamine alkoxylates (TETRONICS—BASF), ethylene oxide/propylene oxide copolymers (PLURONICS—BASF), Gemini type surfactants (Rhodia) and diphenyl ether Gemini type surfactants (e.g. DOWFAX—Dow Chemical).

Preferred surfactants include ethylene oxide/propylene oxide copolymers (EO/PO); amine ethoxylates; alkyl polyglycosides; oxo-tridecyl alcohol ethoxylates, and so forth.

In a preferred embodiment, the agrochemical composition of the present invention further comprises one or more agrochemical ingredients. Suitable agrochemical ingredients include, but not limited to, herbicides, insecticides, growth regulators, fungicides, miticides, acaricides, fertilizers, biologicals, plant nutritionals, micronutrients, biocides, paraffinic mineral oil, methylated seed oils (i.e. methylsoyate or methylcanolate), vegetable oils (such as soybean oil and canola oil), water conditioning agents such as Choice® (Loveland Industries, Greeley, Colo.) and Quest® (Helena Chemical, Collierville, Tenn.), modified clays such as Surround® (BASF), foam control agents, surfactants, wetting agents, dispersants, emulsifiers, deposition aids, antidrift components, and water.

Suitable agrochemical compositions are made by combining, in a manner known in the art, such as, by mixing one or more of the above components with the ester modified organosilicon based surfactant of the present invention, either as a tank-mix, or as an "In-can" formulation. The term "tank-mix" means the addition of at least one agrochemical to a spray medium, such as water or oil, at the point of use. The term "In-can" refers to a formulation or concentrate containing at least one agrochemical component. The "In-can" formulation may then diluted to use concentration at the point of use, typically in a Tank-mix, or it may be used undiluted.

B. Coatings:

Typically coatings formulations will require a wetting agent or surfactant for the purpose of emulsification, compatibilization of components, leveling, flow and reduction of surface defects. Additionally, these additives may provide improvements in the cured or dry film, such as improved abrasion resistance, antiblocking, hydrophilic, and hydrophobic properties. Coatings formulations may exists as, Solvent-borne coatings, water-borne coatings and powder coatings.

The coatings components may be employed as: architecture coatings; OEM product coatings such as automotive coatings and coil coatings; Special Purpose coatings such as industrial maintenance coatings and marine coatings;

Typical resin types include: Polyesters, alkyds, acrylics, epoxies and polyurethanes.

C. Personal Care

In a preferred embodiment, the ester modified organosilicon based surfactant of the present invention comprises, per 100 parts by weight ("pbw") of the personal care composition, from 0.1 to 99 pbw, more preferably from 0.5 pbw to 30 pbw and still more preferably from 1 to 15 pbw of the ester modified organosilicon based surfactant and from 1 pbw to 99.9 pbw, more preferably from 70 pbw to 99.5 pbw, and still more preferably from 85 pbw to 99 pbw of the personal care composition.

The ester modified organosilicon based surfactant compositions of the present invention may be utilized in personal care emulsions, such as lotions, and creams. As is generally known, emulsions comprise at least two immiscible phases one of which is continuous and the other which is discontinuous. Further emulsions may be liquids with varying viscosities or solids. Additionally the particle size of the emulsions may render them microemulsions and, when sufficiently small, microemulsions may be transparent. Further it is also possible to prepare emulsions of emulsions and these are generally known as multiple emulsions. These emulsions may be:

1) aqueous emulsions where the discontinuous phase comprises water and the continuous phase comprises the ester modified organosilicon based surfactant of the present invention;
2) aqueous emulsions where the discontinuous phase comprises the ester modified organosilicon based surfactant of the present invention and the continuous phase comprises water;
3) non-aqueous emulsions where the discontinuous phase comprises a non-aqueous hydroxylic solvent and the continuous phase comprises the ester modified organosilicon based surfactant of the present invention; and
4) non-aqueous emulsions where the continuous phase comprises a non-aqueous hydroxylic organic solvent and the discontinuous phase comprises the ester modified organosilicon based surfactant of the present invention.

As used herein the term "non-aqueous hydroxylic organic compound" means hydroxyl containing organic compounds exemplified by alcohols, glycols, polyhydric alcohols and polymeric glycols and mixtures thereof that are liquid at room temperature, e.g. about 25° C., and about one atmosphere pressure. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a cream or lotion with improved deposition properties and good feel characteristics. It is capable of being blended into formulations for hair care, skin care, antiperspirants, sunscreens, cosmetics, color cosmetics, insect repellants, vitamin and hormone carriers, fragrance carriers and the like.

The personal care applications where the ester modified organosilicon based surfactant of the present invention and the silicone compositions derived therefrom of the present invention may be employed include, but are not limited to, deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, insect repellent and anti-aging products, color cosmetics such as lipsticks, foundations, face powders, eye liners, eye shadows, blushes, makeup, mascaras and drug delivery systems for topical application of medicinal compositions that are to be applied to the skin.

In a preferred embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, volatile silicones, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with the ester modified organosilicon based surfactant. Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions.

In one useful embodiment, an antiperspirant composition comprises the ester modified organosilicon based surfactant of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex gly.

In another useful embodiment, a skin care composition comprises the ester modified organosilicon based surfactant, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylmethane, p-aminobenzoic acid and octyl dimethyl-p-aminobenzoic acid.

In another useful embodiment, a color cosmetic composition, such as, for example, a lipstick, a makeup or a mascara composition comprises the ester modified organosilicon based surfactant, and a coloring agent, such as a pigment, a water soluble dye or a liposoluble dye.

In another useful embodiment, the compositions of the present invention are utilized in conjunction with fragrant materials. These fragrant materials may be fragrant compounds, encapsulated fragrant compounds, or fragrance releasing compounds that either the neat compounds or are encapsulated.

The uses of the compositions of the present invention are not restricted to personal care compositions, other products such as waxes, polishes and textiles treated with the compositions of the present invention are also contemplated.

D. Home Care

Home care applications include laundry detergent and fabric softener, dishwashing liquids, wood and furniture polish, floor polish, tub and tile cleaners, toilet bowl cleaners, hard surface cleaners, window cleaners, antifog agents, drain cleaners, auto-dish washing detergents and sheeting agents, carpet cleaners, prewash spotters, rust cleaners and scale removers.

In one other embodiment herein the ester-modified organosilicon surfactant composition of the present invention is such that the foliar uptake of various agricultural chemicals is faster for applications containing the ester-modified organosilicon having the general formula (I) than that for equivalent applications containing trisiloxane alkoxylate, such as a polyakyleneoxide modified heptamethyl trisiloxane. In one non-limiting embodiment, the foliar uptake of various agricultural chemicals is greater at 2 hours after application, more specifically greater at 4 hours after application. In one more specific embodiment, the foliar uptake of $^{14}$C-Glyphosate-IPA into barnyardgrass (*Echinachloa-crus-galii*) was determined by the method described in the attached Gaskin et al. reference at 2 and 24 hours after treatment (HAT), and was shown to be greater than the $^{14}$C-Glyphosate-IPA treatment without the composition of the present invention.

The following nonrestrictive examples are further illustrative of the invention.

EXAMPLES

Preparation examples for "Poly Ester Silicons" (PES):

Preparation Example 1 (ID: PES-1)

25 g (0.186 moles) of dimethyl propionic acid with 0.1 g of conc. sulphuric acid and 25 g (1.47 moles) of water were charged into a 4-neck flask attached with a mechanical stirrer, nitrogen inlet. This mixture was quickly heated at 115° C. The oligomerization of dimethyl propionic acid was monitored by 1H NMR. After the average degree of oligomerization became 1.5, the flask was quickly cooled to below 80° C. Immediately, a mixture of 0.5 g of triethylamine and 34.11 g (0.124 moles) of 2-{3-[Dimethyl-(2-trimethylsilanyl-ethyl)-silanyl]-propoxymethyl}-oxirane were charged via an addition funnel. Then reaction mixture was then initially stirred for 18 h at 90° C. and finally 110° C. for 2 h.

After this, the reaction mixture was kept under vacuum (5 torr) at 50° C. for ~2 h to remove the volatiles. A light brown highly viscous polymer (61% solids) was obtained. Analysis by $^1$H-NMR indicated conversion of the epoxy group to ester was 100%, with an average of oligomerization of 1.5 ester units.

General Structure:

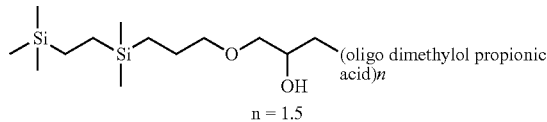

n = 1.5

Preparation Example 2 (ID: CSE-2)

25 g (0.186 moles) of dimethyl propionic acid with 0.1 g of conc. sulphuric acid and 6.25 g (0.367 moles) of water were charged into a 4-neck flask attached with a mechanical stirrer, nitrogen inlet. This mixture was quickly heated at 115° C. The oligomerization of dimethyl propionic acid was monitored by $^1$H-NMR as mentioned above. After the average degree of oligomerization of 3.5 ester units was achieved, the flask was quickly cooled to below 80° C. Immediately, a mixture of 0.5 g of triethylamine and 14.6 g (0.053 moles) of 2-{3-[Dimethyl-(2-trimethylsilanyl-ethyl)-silanyl]-propoxymethyl}-oxirane were charged via an addition funnel. Then reaction mixture was then initially stirred for 18 h at 90° C. and finally 110° C. for 2 h.

After this, the reaction mixture was kept under vacuum (5 torr) at 50° C. for ~2 h to remove the volatiles. A light brown highly viscous polymer (95% solids) was obtained. Analysis by $^1$H-NMR indicated conversion of the epoxy group to ester was 100%, with an average of oligomerization of 3.5 ester units.

General Structure:

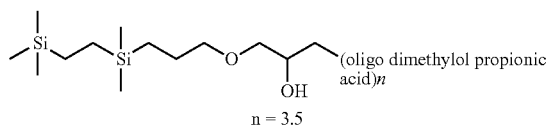

n = 3.5

Preparation Example 3 (ID: PES-3)

25 g (0.186 moles) of dimethyl propionic acid with 0.1 g of conc. sulphuric acid and 2.78 g (0.163 moles) of water were charged into a 4-neck flask attached with a mechanical stirrer, nitrogen inlet. This mixture was quickly heated at 115° C. The oligomerization of dimethyl propionic acid was monitored by $^1$H-NMR. After the average degree of oligomerization of 4.5 was achieved, the flask was quickly cooled to below 80° C. Immediately, a solution of 0.5 g of triethylamine and 11.37 g (0.041 moles) of 2-{3-[Dimethyl-(2-trimethylsilanyl-ethyl)-silanyl]-propoxymethyl}-oxirane were charged via an addition funnel. Then reaction mixture was then initially stirred for 18 h at 90° C. and finally 110° C. for 2 h.

After this, the reaction mixture was kept under vacuum (5 torr) at 50° C. for ~2 h to remove the volatiles. A light brown highly viscous polymer (94% solids) was obtained. Analysis by $^1$H-NMR indicated conversion of the epoxy group to ester was 100%, with an average of oligomerization of 4.5 ester units.

General Structure:

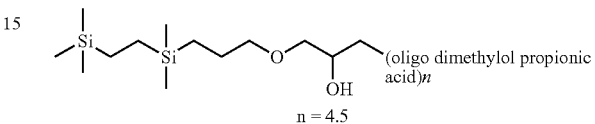

n = 4.5

Preparation Example 4 (ID: PES-4)

25 g (0.186 moles) of dimethyl propionic acid with 0.1 g of conc. sulphuric acid and 1.32 g (0.078 moles) of water were charged into a 4-neck flask attached with a mechanical stirrer, nitrogen inlet. This mixture was quickly heated at 115° C. The oligomerization of dimethyl propionic acid was monitored by 1H NMR as mentioned above. After the average degree of oligomerization became 6, the flask was quickly cooled to below 80° C. Immediately, a solution of 0.5 g of triethylamine and 8.53 g (0.031 moles) of 2-{3-[Dimethyl-(2-trimethylsilanyl-ethyl)-silanyl]-propoxymethyl}-oxirane were charged via an addition funnel. Then reaction mixture was then initially stirred for 18 h at 90° C. and finally 110° C. for 2 h.

After this, the reaction mixture was kept under vacuum (5 torr) at 50° C. for ~2 h to remove the volatiles. A light brown highly viscous polymer (97% solids) was obtained. Analysis by $^1$H-NMR indicated conversion of the epoxy group to ester was 100%, with an average of oligomerization of 6 ester units.

Approximate Structure:

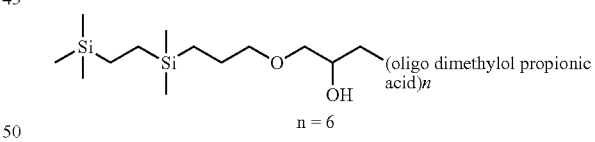

n = 6

Comparative Surfactants

Comp-A: $(CH_3)_3$—Si—$CH_2CH_2Si(CH_3)_2$—K
Comp-B $(CH_3)_3$—Si—O—$Si(CH_3)(K)O$—Si—$(CH_3)_3$
where K=: —$C_3H_2O(CH_2CH_2O)_8CH_3$ Results Example 1 Spreading Properties Spreading of the surfactants compositions was determined by applying a 10 µL droplet of the desired aqueous solution (0.1% w/v) to the bottom half of a polystyrene Petri dish. The spread diameter (mm) was recorded after 30 seconds.

Table-1 demonstrates that within each set, spreading increased with an increase in surfactant concentration. Additionally, as the number of ester units increased there was a corresponding decrease in spreading, with the exception of PES-4 containing 6 ester units, implying that phase behavior, or overall solubility, may also play a role in spreading.

TABLE 1

Spreading Properties of Ester Modified Organosilicon Surfactants

| ID | Ester Units | Concentration | | | |
|---|---|---|---|---|---|
| | | 0.20% | 0.10% | 0.05% | 0.025% |
| PES-1 | 1.5 | 27 | 18 | 10 | 8 |
| PES-2 | 3.5 | 6 | 6 | 5 | 4 |
| PES-3 | 4.5 | 7 | 5 | 5 | 5 |
| PES-4 | 6.0 | 14 | 7 | 7 | 6 |
| Comp-A | NA | 54 | 43 | 30 | nd |

Example 2—Surface Tension of Ester Modified Organosilicon Surfactants

The ability to reduce aqueous surface tension is an important factor for surfactants used in agricultural formulations. The surface tension as a function of concentration was determined for the compositions of the present invention relative to Comp-A. The Ester Modified Organosilicon surfactants (PES-1 to PES-4) and Comp-A are based on the same hydrophobic group:

$(CH_3)_3$—Si—$CH_2CH_2Si(CH_3)_2$—.

The main difference is the hydrophilic group, which for Comp-A is polyethyleneoxide [—$C_3H_2O(CH_2CH_2O)_8$ $CH_3$], while the hydrophilic group for PES compositions is based on oligo dimethylol propionic acid, as shown above in Preparative examples 1-4.

Surface tension was measured using the Wilhelmy Plate method. Solutions of the various compositions were prepared in deionized water. Table 2 demonstrates that although the hydrophilic group on the PES compositions is based on a polyester, rather than polyethyleneoxide, compositions of the present invention are capable of reducing aqueous surface tension to the low to mid 20's mN/m. Overall these materials gave a lower surface tension than Comp-A at the typical use levels (0.1% to 1%). Additionally most of the PES compositions had a lower critical micelle concentration (CMC) than Comp-A.

TABLE 2

Surface Tension of Ester Modified Organosilicon Surfactants

| Wt % Actives | Surface Tension (mN/m) | | | | |
|---|---|---|---|---|---|
| | PES-1 | PES-2 | PES-3 | PES-4 | Comp-A |
| 1.0 | 22.0 | 23.0 | 23.9 | 24.2 | 23.7 |
| 0.1 | 23.8 | 23.8 | 25.3 | 24.5 | 24.4 |
| 0.01 | 25.1 | 94.3 | 26.5 | 26.0 | 25.4 |
| 0.003 | 27.1 | 26.5 | 29.9 | 28.5 | 30.1 |
| 0.001 | 30.4 | 35.3 | 38.0 | 32.8 | 34.8 |
| 0.0001 | 59.4 | 56.3 | 59.7 | 42.5 | 48.7 |
| 0.00001 | 65.0 | 69.4 | 66.4 | 60.5 | 62.4 |
| CMC (wt %): | 0.0018 | 0.0042 | 0.0043 | 0.0062 | 0.005 |
| Polyester Units: | 1.5 | 3.5 | 4.5 | 6 | NA |

Example 3-Effect of Adjuvant on Uptake of $^{14}$C-Glyphosate Isopropylamine Salt into Barnyardgrass This example compares the impact of the surfactants hydrophilic group (Polyethyleneoxide group vs. Ester group) on uptake of the herbicide glyphosate (0.75%), into Barnyardgrass (Echinachloa-crus-galii). It is important to note that the Ester Modified Organosilicon surfactants of the present invention (PES-1, PES-3 and PES-4) and Comp-A are based on the exact same hydrophobic group [i.e. $(CH_3)_3$—Si—$CH_2CH_2Si(CH_3)_2$— ], but use different hydrophilic groups.

Uptake was determined according to the method described in the Gaskin et al. 1993. Pestic. Sci. 38: 185-192, where reference, at 2 and 24 hours after treatment (HAT). Using a microsyringe, ten 0.24 μl drops, of radio-labeled herbicide, $^{14}$C-Glyphosate-isopropylamine (GLY) solution are applied to the adaxial surface of the youngest fully expanded leaf on each plant. Uptake is assessed by washing the treated leaf surface with a water-ethanol (1:1) solution to recover unabsorbed radio-labeled herbicide, and quantified by liquid scintillation counting. Uptake is calculated as a percentage of $^{14}$C-labeled herbicide not recovered relative to the applied dose.

TABLE 3

Effect of Hydrophilic Group on Uptake of $^{14}$C-GLY into Barnyardgrass

| ID | Hydrophile | | Uptake (%)[1] | |
|---|---|---|---|---|
| | Type | DP | 2 HAT | 24 HAT |
| PES-1 | Polyester | 1.5 | 33.6 f | 56.2 c |
| PES-3 | Polyester | 4.5 | 38.7 e | 62.0 b |
| PES-4 | Polyester | 6 | 53.7 cd | 76.9 a |
| Comp-A | Polyethyleneoxide | 8 EO | 18.0 g | 49.0 d |

Note
1: Means sharing common postscripts are not statistically different (p = 0.05)

Table 3 demonstrates that the compositions of the present invention unexpectedly provided a significant improvement in uptake of glyphosate-IPA into Barnyardgrass relative to comparative material (Comp-A) at 2 HAT and 24 HAT.

Example 4—Effect of Adjuvant on Gly-IPA Solution Droplet Adhesion and Total Available Dose into Barnyardgrass The effect of adjuvant on the droplet adhesion and total available dose of the herbicide, glyphosate-isopropylamine at 1% a.e. (Gly-IPA) was determined on Barnyardgrass (Echinochloa crus-galli) leaf surface.

Spray droplet adhesion (as a % of impacted droplets) was determined using a piezoelectric droplet generator with a 200 μm nozzle orifice to form mono-sized droplets of approx. 400 μm (Stevens et al. 1993). The droplet freefall distance was 14 cm. Barnyardgrass (BYDG) leaf surface is very difficult-to-wet. Contact angle (20% aqueous acetone) on the adaxial surface of the leaf is 180°. Droplets were impacted from a height of 14 cm, to leaves mounted horizontally.

Table 4 demonstrates that the ester-modified organosilicon compositions of the present invention provided similar or better droplet adhesion on BYDG relative to the comparative adjuvant.

Likewise, the actual amount of agrochemical that gets to the leaf surface is dependent on droplet adhesion. Therefore we can calculate the amount of Gly-IPA that is delivered for uptake by taking into consideration the level of Uptake and Adhesion, as the "Total Available Dose" (TAD). This is represented as: TAD=Uptake % X Adhesion %. The higher the TAD, the greater the amount of Gly-IPA delivered into the BYDG.

Table 4 also demonstrates that the EO-Free, ester-modified organosilicon compositions of the present invention provided equivalent or better performance than the EO-containing Comp-A. Wherein PES-1 and PES 3 significantly increased in droplet adhesion and TAD. PES-4 gave a higher level of uptake relative to Comp-A, however both products had a low level of adhesion.

TABLE 4

Effect of Adjuvant on Total Available Dose

| ID | No. Polyester Units | Uptake: Gly-IPA[1.] 2 hat | Uptake: Gly-IPA[1.] 24 hat | Adhesion (%) | TAD (2 h) | TAD (24 h) |
|---|---|---|---|---|---|---|
| PES-1 | 1.5 | 33.6 c | 56.2 c | 45 b | 15 | 25 |
| PES-3 | 4.5 | 38.7 b | 62.0 b | 52 a | 20 | 32 |
| PES-4 | 6 | 53.7 a | 76.9 a | 12 d | 6 | 9 |
| Comp-A[2.] | NA | 18.0 d | 49.0 d | 22 c | 4 | 11 |

Note:
[1.]Within columns, means sharing common postscripts are not statistically different (LSD test, P = 0.05)
[2.]Comp A is based on carbosilane modified with polyethyleneoxide as the hydrophile (~8EO, methyl capped; see section on Comparative Surfactants)

While the invention has been described with reference to a number of exemplary embodiments, it will be understood by those skilled in the art that various changes can be made and equivalents can be substituted for elements thereof without departing from the scope of the invention. In addition, many modifications can be made to adapt a particular situation or material to the teachings of the invention without departing from essential scope thereof. Therefore, it is intended that the invention not be limited to any particular exemplary embodiment disclosed herein.

What is claimed is:

1. A polyalkylene-oxide-free surfactant composition comprising an ester-modified organosilicon having the formula (I):

$$AO_a R^4{}_b (BO_c R^{11}{}_d)_e (C)_f D_g \qquad (I)$$

where
A=$R^1 R^2 R^3$Si—
B=—Si($R^5$)($R^6$)—
C=$R^7 R^8 R^9$Si—
D=—O($R^{14}$)$_p R^{19}$
where $R^4$ and $R^{11}$ are each independently selected from a branched or linear divalent hydrocarbon radical of 1 to 12 carbons, subscripts a, b, c, d, e, f, g and p are each 0 or 1 and subject to the following provisos:
a+b=1; when e=1, c+d=1; and, when g=1, then a+e+f=0;
$R^1$ $R^2$ $R^3$ $R^5$ $R^7$ $R^8$ are each independently selected from the group consisting of monovalent hydrocarbon radicals having from 1 to 8 carbon atoms, and an aryl or alkaryl hydrocarbon radical of from 6 to 12 carbon atoms, and $R^{10}$;
where each $R^{10}$ is independently selected from the group consisting of branched monovalent hydrocarbon radicals of from 3 to 6 carbon atoms;
$R^6$ and $R^9$ are each independently selected from the group consisting of linear or branched monovalent hydrocarbon radicals containing from 1 to 8 carbon atoms, and $R^{12}$, provided that in formula (I) $R^6$ and $R^9$ are different and one of $R^6$ and $R^9$ is $R^{12}$,
wherein $R^{12}$ is —$R^{13}$O($R^{14}$)$_p R^{19}$ or a cyclohexyl group of the formula (Q):

<br>

$$\text{\textasciitilde\textasciitilde\textasciitilde} CH_2 - \underset{R^{15}}{\underset{|}{C}} H - \text{cyclohexyl}(R^{16}, R^{17}, R^{18}) \qquad (Q)$$

where $R^{13}$ is selected from a branched or linear divalent hydrocarbon radical containing from 3 to 12 carbon atoms, which is optionally —OH substituted;
$R^{14}$ is selected from —$CH_2CH(R^{20})CH_2O$—, —$CH_2(CH_2)_xCH(R^{20})CH_2O$—, and a bridging group of the formula (Y):

$$-[C_2H_4O]_h-[C_3H_6O]_i-[C_4H_8O]_j-[C_2H_4O]_k-[CH_2CH(R^{20})CH_2O]_n- \qquad (Y);$$

wherein subscripts h, i, j, and k are zero or one and satisfy the following relationships:
0≤h+i+j+≤1, and 0≤h+k≤1
$R^{20}$ is H, OH or —$OR^{19}$,
subscript x is from 1 to 9,
subscripts p and n are 0 or 1, and
$R^{15}$ and $R^{16}$ are each independently selected from H or methyl;
$R^{17}$ and $R^{18}$ are each independently selected from OH or —$OR^{19}$; provided that in formula (Q) $R^{17}$ and $R^{18}$ are the same or different, and at least one of $R^{17}$ and $R^{18}$ is $OR^{19}$,
where $R^{19}$ is derived from the esterification of the corresponding hydroxy carboxylic acid or a mixture of corresponding hydroxy carboxylic acids, which hydroxy carboxylic acid(s) contain(s) from 2 to 8 carbon atoms,
and where $R^{19}$ is of the formula (Z):

$$-C(=O)-CR^{21}R^{22}R^{23} \qquad (Z)$$

where $R^{21}$, $R^{22}$, $R^{23}$ are each independently selected from H, —OH, —$CH_2OH$, —OZ, —$(R^{24})_mO-R^{27}$, —$CH_3$, —$CH_2CH_3$, and —$(R^{24})_mO-C(=O)(CR^{25}R^{26})_t CH_2OR^{27}$
where $R^{24}$ is a divalent hydrocarbon radical of 1 to 3 carbon atoms,
$R^{25}$ and $R^{26}$ are each independently selected from H, —OH, —$CH_2OH$, —OZ, —$(R^{24})_mO-R^{27}$, —$CH_3$, —$CH_2CH_3$, and —$(R^{24})_mO-C(=O)-(CR^{25}R^{26})_t CH_2OR^{27}$
$R^{27}$ is independently selected from H, Z, —$CH_2OH$, —$CH_3$, —$CH_2CH_3$, and [—C(=O)(CR^{25}R^{26})_t CH_2O]_w-R^{29}$,
$R^{29}$ is independently selected from H, —$CH_2OH$, —$CH_3$, and —$CH_2CH_3$
subscript m is 0 to 3, t is 1 to 5 and w is 1 to 5; the number of Z groups in $R^{19}$ is between 1 and 10; and, provided that when any one or more of $R^{21}$, $R^{22}$ and $R^{23}$ are of the formula —$(R^{24})_mO-C(=O)-(CR^{25}CR^{26})_t CH_2OR^{27}$ that $R^{21}$, $R^{22}$ or $R^{23}$ group contains from 1 to 10 —$(R^{24})_mO-C(=O)-(CR^{25}CR^{26})_t CH_2OR^{27}$ groups; and
provided that ester-modified organosilicon having the formula (I) contains an $R^{19}$ group.

2. The composition of claim 1 wherein the ester-modified organosilicon is of the formula (II):

$$AOC \quad (II)$$

wherein:
A=$R^1R^2R^3Si$—
C=$R^7R^8R^9Si$—
wherein each of $R^2$, $R^3$, $R^7$ and $R^8$ are methyl,
$R^1$ is a neo-hexyl group containing six carbon atoms,
$R^9$ is $R^{12}$, where $R^{12}$ is —$R^{13}O(R^{14})_pR^{19}$
where —$R^{13}$ is a divalent hydrocarbon radical having 3 carbon atoms,
$R^{14}$ is —$CH_2CH(R^{20})CH_2O$—,
$R^{20}$ is OH,
$R^{19}$ is —C(=O)—$CR^{21}R^{22}R^{23}$ formula (Z),
where $R^{22}$ is methyl
$R^{21}$ and $R^{23}$ are —$(R^{24})_mO$—$R^{27}$,
where $R^{24}$ is a divalent hydrocarbon of 1 to 3 carbon atoms,
$R^{27}$ is Z or H, providing that
the number of Z groups in $R^{19}$ is about 3 to 4,
subscripts m and p are 1; and,
the hydroxy acid is selected from dimethylol propionic acid, glycolic acid, gluconic acid and lactic acid.

3. The composition of claim 1 wherein the ester-modified organosilicon is of the formula (III):

$$AR^4C \quad (III)$$

wherein
A=$R^1R^2R^3Si$—
C=$R^7R^8R^9Si$—
where $R^1$, $R^2$, $R^3$, $R^7$ and $R^8$ are methyl,
$R^4$ is —$CH_2CH_2$—,
$R^9$ is $R^{12}$, where $R^{12}$ is —$R^{13}O(R^{14})_pR^{19}$
where —$R^{13}$ is a divalent hydrocarbon radical having 3 carbon atoms,
$R^{14}$ is —$CH_2CH(R^{20})CH_2O$—,
$R^{20}$ is OH,
$R^{19}$ is —C(=O)—$CR^{21}R^{22}R^{23}$ formula (Z),
where $R^{22}$ is methyl
$R^{21}$ and $R^{23}$ are —$(R^{24})_mO$—$R^{27}$,
where $R^{24}$ is a divalent hydrocarbon of 1 to 3 carbon atoms,
$R^{27}$ is Z or H, providing that the number of Z groups in $R^{19}$ is about 3 to 4;
subscripts m and p are 1; and,
the hydroxy acid is selected from dimethylol propionic acid, glycolic acid, gluconic acid and lactic acid.

4. The composition of claim 1 wherein the ester-modified organosilicon is of the formula (IV):

$$AR^4BOC \quad (IV)$$

wherein
A=$R^1R^2R^3Si$—
B=—$Si(R^5)(R^6)$—
C=$R^7R^8R^9Si$—
$R^1$, $R^2$, $R^3$, $R^7$ and $R^8$ are methyl,
$R^4$ is —$CH_2CH_2$—, $R^5$ is selected from the group consisting of a monovalent hydrocarbon radical having from 1 to 8 carbon atoms, and an aryl or alkaryl hydrocarbon radical of from 6 to 12 carbon atoms, and $R^{10}$, where $R^{10}$ is selected from the group consisting of branched monovalent hydrocarbon radicals of from 3 to 6 carbon atoms, $R^6$ is selected from the group consisting of linear or branched monovalent hydrocarbon radicals containing from 1 to 8 carbon atoms,
$R^9$ is $R^{12}$, where $R^{12}$ is —$R^{13}O(R^{14})_pR^{19}$
where —$R^{13}$ is a divalent hydrocarbon radical having 3 carbon atoms,
$R^{14}$ is —$CH_2CH(R^{20})CH_2O$—,
$R^{20}$ is OH,
$R^{19}$ is —C(=O)—$CR^{21}R^{22}R^{23}$ formula (Z),
where $R^{22}$ is methyl,
$R^{21}$ and $R^{23}$ are —$(R^{24})_mO$—$R^{27}$,
where $R^{24}$ is a divalent hydrocarbon of 1 to 3 carbon atoms,
$R^{27}$ is Z or H, providing that the number of Z units in $R^{19}$ is about 4 to 6,
subscripts m and p are 1; and,
the hydroxy acid is selected from dimethylol propionic acid, glycolic acid, gluconic acid and lactic acid.

5. The composition of claim 1 wherein the ester-modified organosilicon is of the formula (V):

$$AR^4C \quad (V)$$

wherein
A=$R^1R^2R^3Si$—
C=$R^7R^8R^9Si$—
$R^1$, $R^2$, $R^3$, $R^7$ and $R^8$ are methyl,
$R^4$ is —$CH_2CH_2$—,
$R^9$ is $R^{12}$, where $R^{12}$ is —$R^{13}OR^{19}$
where —$R^{13}$ is a divalent hydrocarbon radical having 3 carbon atoms,
$R^{19}$ is —C(=O)—$CR^{21}R^{22}R^{23}$ formula (Z),
wherein $R^{21}$ and $R^{23}$ are H,
$R^{22}$ is —$(R^{24})_mO$—$R^{27}$,
where $R^{24}$ is a divalent hydrocarbon of 1 to 3 carbon atoms,
$R^{27}$ is Z or H providing that the number of Z groups in $R^{19}$ is about 4 to 5,
subscript m is 1; and,
the hydroxy acid is selected from dimethylol propionic acid, glycolic acid, gluconic acid and lactic acid.

6. The composition of claim 1 wherein the ester-modified organosilicon is of the formula (VI):

$$AOBOC \quad (VI)$$

wherein,
A=$R^1R^2R^3Si$—
B=—$Si(R^5)(R^6)$—
C=$R^7R^8R^9Si$—
$R^1$, $R^2$, $R^3$, $R^7$, $R^8$ and $R^9$ are methyl $R^5$ is selected from the group consisting of a monovalent hydrocarbon radical having from 1 to 8 carbon atoms, and an aryl or alkaryl hydrocarbon radical of from 6 to 12 carbon atoms, and $R^{10}$, where $R^{10}$ is selected from the group consisting of branched monovalent hydrocarbon radicals of from 3 to 6 carbon atoms,
$R^6$ is $R^{12}$, where $R^{12}$ is —$R^{13}O(R^{14})_pR^{19}$
where —$R^{13}$ is a divalent hydrocarbon radical having 3 carbon atoms,
$R^{14}$ is —$CH_2CH(R^{20})CH_2O$—,
$R^{20}$ is OH,
$R^{19}$ is —C(=O)—$CR^{21}R^{22}R^{23}$ formula (Z),
where $R^{22}$ is methyl,
$R^{21}$ and $R^{23}$ are —$(R^{24})_mO$—$R^{27}$,
where $R^{24}$ is a divalent hydrocarbon of 1 to 3 carbon atoms,
$R^{27}$ is Z or H providing that the number of Z groups in $R^{19}$ is about 4 to 6,
subscripts m and p are each 1; and,
the hydroxy acid is selected from dimethylol propionic acid, glycolic acid, gluconic acid and lactic acid.

7. The composition of claim 1 wherein the ester-modified organosilicon is of the formula (VII):

$$AR^4D \quad (VII)$$

wherein
$A=R^1R^2R^3Si-$
$R^4$ is a divalent hydrocarbon radical of 6 carbon atoms;
$D=-O(R^{14})_pR^{19}$
where $R^1$, $R^2$ and $R^3$ are each methyl;
$R^{14}$ is $-CH_2CH(R^{20})CH_2O-$
where $R^{20}$ is OH;
$R^{19}$ is $-C(=O)-CR^{21}R^{22}R^{23}$ formula (Z),
where $R^{22}$ is methyl;
$R^{21}$ and $R^{23}$ are $-(R^{24})_mO-R^{27}$,
where $R^{24}$ is a divalent hydrocarbon of 1 to 3 carbon atoms,
$R^{27}$ is Z or H, providing that the number of Z groups in $R^{19}$ is about 3 to 6,
the subscripts m and p are each 1; and,
the hydroxy acid is selected from dimethylol propionic acid, glycolic acid, gluconic acid and lactic acid.

8. The composition of claim 1 wherein the ester-modified organosilicon is of the formula (VIII):

$$AR^4C \quad (VIII)$$

wherein
$A=R^1R^2R^3Si-$
$C=R^7R^8R^9Si-$
$R^1$, $R^2$, $R^3$, $R^7$ and $R^8$ are methyl,
$R^4$ is $-CH_2CH_2-$
$R^9$ is $R^{12}$ of the formula (Q)

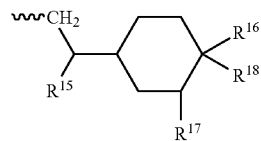

(Q)

where
$R^{15}$ and $R^{16}$ are methyl
$R^{17}$ and $R^{18}$ are $-OH$ or $-OR^{19}$; provided that in (Q) $R^{17}$ and $R^{18}$ are the same or different, and at least one of these substituents is $OR^{19}$,
$R^{19}$ is of the formula (Z): $-C(=O)-CR^{21}R^{22}R^{23}$ (Z),
wherein $R^{21}$ and $R^{23}$ are H,
$R^{22}$ is $-(R^{24})_mO-C(=O)(CR^{25}R^{26})_tCH_2OR^{27}$
where $R^{24}$ is a divalent hydrocarbon of 1 to 3 carbon atoms,
$R^{25}$ and $R^{26}$ are H, $-OH$, or $-(R^{24})_mO-C(=O)-(CR^{25}R^{26})_tCH_2OR^{27}$
$R^{27}$ is H, or $[-C(=O)(CR^{25}R^{26})_tCH_2O]_w-R^{29}$,
$R^{29}$ is H, providing that the number of Z groups in $R^{19}$ is about 3 to 4;
t is 4 or 5, m is 1, and w is 2 to 3, provided that $R^{22}$ has from 1 to 10 $-(R^{24})_mO-C(=O)-(CR^{25}CR^{26})_tCH_2OR^{27}$ groups.

9. A method of making the ester-modified organosilicon having the formula (I) of claim 1 comprising:
reacting a corresponding hydride intermediate with an olefinically-modified intermediate in the presence of a catalyst,
wherein the corresponding hydride intermediate is of the formula (I-a):

$$AO_aR^4{}_b(B^HO_cR^{11}{}_d)_eC^H \quad (I\text{-}a)$$

wherein:
$A=R^1R^2R^3Si-$;
$B^H=-Si(R^5)(R^{6H})-$;
$C^H=R^7R^8R^{9H}Si-$;
subscripts a, b, c, d and e are each 0 or 1 and subject to the following provisos: a+b=1 and when e=1, c+d=1;
$R^1$, $R^2$, $R^3$, $R^5$, $R^7$, $R^8$ are each independently selected from the group consisting of monovalent hydrocarbon groups containing from 1 to 8 carbon atoms, and monovalent aryl and alkaryl hydrocarbon groups containing from 6 to 12 carbon atoms, and $R^{10}$,
wherein $R^{10}$ is selected from a group consisting of branched monovalent hydrocarbon groups of containing from 3 to 6 carbon atoms;
$R^4$ and $R^{11}$ are each independently selected from the group consisting of a divalent hydrocarbon group containing from 1 to 4 carbon atoms;
$R^{6H}$ and $R^{9H}$ are independently selected from the group consisting of linear or branched monovalent hydrocarbon groups containing from 1 to 8 carbon atoms, and hydrogen,
provided that in formula (I-a), $R^{6H}$ and $R^{9H}$ are different and at least one $R^{6H}$ or $R^{9H}$ is hydrogen, and
wherein the olefinically-modified intermediate possesses one or more oxirane or oxetane groups and contains one or more terminal or pendant carbon-carbon double bonds and contains from 4 to 12 carbon atoms,
to produce an epoxy-modified organosilicon intermediate; and,
adding the epoxy-modified organosilicon intermediate to a carboxylic acid-terminated oligomer in the presence of a catalyst,
wherein the carboxylic acid-terminated oligomer is made by esterifying the carboxylic acid group of a hydroxy carboxylic acid with a hydroxy group of the same or a different hydroxy carboxylic acid, wherein the hydroxy carboxylic acid(s) contain from 2 to 8 carbon atoms,
to produce the ester-modified organosilicon having the formula (I).

10. A method of making the ester-modified organosilicon having the formula (I) of claim 1 comprising:
reacting a corresponding hydride intermediate with a olefinically-modified intermediate in the presence of a catalyst,
wherein the corresponding hydride intermediate is selected from the group of consisting of formulae (I-a):

$$AO_aR^4{}_b(B^HO_cR^{11}{}_d)_eC^H \quad (I\text{-}a)$$

wherein:
$A=R^1R^2R^3Si-$;
$B^H=-Si(R^5)(R^{6H})-$;
$C^H=R^7R^8R^{9H}Si-$;
subscripts a, b, c, d and e are each 0 or 1 and subject to the following provisos: a+b=1 and when e=1, c+d=1;
$R^1$, $R^2$, $R^3$, $R^5$, $R^7$, $R^8$ are each independently selected from the group consisting of monovalent hydrocarbon groups containing from 1 to 8 carbon atoms, monovalent aryl and alkaryl hydrocarbon groups containing from 6 to 12 carbon atoms, and $R^{10}$,
wherein $R^{10}$ is selected from the group consisting of branched monovalent hydrocarbon groups containing from 3 to 6 carbon atoms;
$R^4$ and $R^{11}$ are each independently selected from the group consisting of a divalent hydrocarbon group containing from 1 to 4 carbon atoms;

$R^{6H}$ and $R^{9H}$ are each selected from the group consisting of linear or branched monovalent hydrocarbon groups containing from 1 to 8 carbon atoms, and hydrogen, provided that in formula (I-a), $R^{6H}$ and $R^{9H}$ are different, and at least one of $R^{6H}$ or $R^{9H}$ is hydrogen, and wherein the olefinically-modified intermediate possesses one or more oxirane or oxetane groups and contains one or more terminal or pendant carbon-carbon double bonds and contains from 4 to 12 carbon atoms, to produce an epoxy-modified organosilicon intermediate; and, reacting one equivalent of the epoxy-modified organosilicon intermediate with one equivalent of hydroxyl carboxylic acid wherein the hydroxy carboxylic acid(s) contain from 2 to 8 carbon atoms, in the presence of a catalyst to produce the ester-modified organosilicon having the formula (I).

11. The method of claim 10 wherein the ester-modified organosilicon having the formula (I), is such that it contains pendant hydroxyl groups and wherein the method further comprises esterifying the pendant hydroxyl groups with further hydroxy carboxylic acid in the presence of acid catalyst, and then the neutralizing the reaction product with an organic base.

12. A method of making the ester-modified organosilicon having the formula (I) of claim 1 comprising:

esterifying the carboxylic acid group of a hydroxy carboxylic acid with the hydroxy group of the same or a different hydroxy carboxylic acid, wherein the hydroxy carboxylic acid(s) contain from 2 to 8 carbon atoms to produce a carboxylic acid-terminated oligomer and reacting the carboxylic acid-terminated oligomer with a hydroxy-modified organosilicon intermediate to produce the ester-modified organosilicon of formula (I)

wherein the hydroxy-modified organosilicon intermediate is produced by reacting free carboxylic acid oligomer with an epoxy-modified organosilicon intermediate, wherein the epoxy-modified organosilicon intermediate is made by hydrosilylating an olefinically-modified intermediate possessing one or more oxirane or oxetane groups and containing one or more terminal or pendant carbon-carbon double bonds and containing from 4 to 12 carbon atoms prior to hydrosilyation, with a hydride intermediate which is of the formula (I-a):

$$AO_a R^4{}_b (B^H O_c R^{11}{}_d)_e C^H \qquad \text{(I-a)}$$

wherein:
$A = R^1 R^2 R^3 Si-$;
$B^H = -Si(R^5)(R^{6H})-$;
$C^H = R^7 R^8 R^9 Si-$;

subscripts a, b, c, d and e are each 0 or 1 and subject to the following provisos: a+b=1 and when e=1, c+d=1;

$R^1$, $R^2$, $R^3$, $R^5$, $R^7$, $R^8$ are each independently selected from the group consisting of monovalent hydrocarbon groups containing from 1 to 8 carbon atoms, and monovalent aryl and alkaryl hydrocarbon groups containing from 6 to 12 carbon atoms, and $R^{10}$, wherein $R^{10}$ is selected from the group consisting of branched monovalent hydrocarbon groups containing from 3 to 6 carbon atoms;

$R^4$ and $R^{11}$ are each independently selected from the group consisting of a divalent hydrocarbon group containing from 1 to 4 carbon atoms;

$R^{6H}$ and $R^{9H}$ are each selected from the group consisting of linear or branched monovalent hydrocarbon groups containing from 1 to 8 carbon atoms, and hydrogen, provided that in formula (I-a), $R^{6H}$ and $R^{9H}$ are different, and at least one of $R^{6H}$ or $R^{9H}$ is hydrogen.

13. A method of making the ester-modified organosilicon having the formula (I) of claim 1 comprising:

reacting one equivalent of hydroxy carboxylic acid with one equivalent of hydroxy-modified organosilicon intermediate in the presence of catalyst, wherein wherein the hydroxy-modified organosilicon intermediate is produced by reacting free carboxylic acid oligomer with epoxy-modified organosilicon intermediate, wherein the epoxy-modified organosilicon intermediate is made by hydrosilylating olefinically modified intermediate possessing one or more oxirane or oxetane groups and containing one or more terminal or pendant carbon-carbon double bonds and containing from 4 to 12 carbon atoms prior to hydrosilyation with a hydride intermediate which is selected from the group of consisting of formulae (I-a)-(IV-a), (VI-a) and (VII-a):

$$AO_a R^4{}_b (B^H O_c R^{11}{}_d)_e C^H \qquad \text{(I-a)}$$

$$AOC^H \qquad \text{(II-a)}$$

$$AR^4 C^H \qquad \text{(III-a)}$$

$$AR^4 B^H OC^H \qquad \text{(IV-a)}$$

$$AOB^H OC^H \qquad \text{(VI-a)}$$

$$AR^4 D^H \qquad \text{(VII-a)}$$

wherein:
$A = R^1 R^2 R^3 Si-$;
$B^H = -Si(R^5)(R^{6H})-$;
$C^H = R^7 R^8 R^9 Si-$; and,
$D^H = AR^{4H}$ subscripts a, b, c, d and e are each 0 or 1 and subject to the following provisos: a+b=1 and when e=1, c+d=1;

$R^1$, $R^2$, $R^3$, $R^5$, $R^7$, $R^8$ are each independently selected from the group consisting of monovalent hydrocarbon groups containing from 1 to 8 carbon atoms, monovalent aryl and alkaryl hydrocarbon groups containing from 6 to 12 carbon atoms, and $R^{10}$, wherein $R^{10}$ is selected from a group consisting of branched monovalent hydrocarbon groups of containing from 3 to 6 carbon atoms;

$R^4$ and $R^{11}$ are each independently selected from the group consisting of a divalent hydrocarbon group containing from 1 to 4 carbon atoms;

$R^{4H}$ is a linear or branched monovalent hydrocarbon radical of 1 to 12 carbon atoms;

$R^{6H}$ and $R^{9H}$ are independently selected from the group consisting of linear or branched monovalent hydrocarbon groups containing from 1 to 8 carbon atoms, and hydrogen, provided that in formulae (I-a), (IV-a) and (VI-a), $R^{6H}$ and $R^{9H}$ are different and at least one $R^{6H}$ or $R^{9H}$ is hydrogen, to produce the ester-modified organosilicon having the formula (I).

14. The method of claim 13 wherein the ester-modified organosilicon having the formula (I), is such that it contains pendant hydroxyl groups and wherein the method further comprises esterifying the pendant hydroxyl groups with further hydroxy carboxylic acid in the presence of acid catalyst, and then the neutralizing the reaction product with an organic base.

15. A method of making the ester-modified organosilicon having the formula (I) of claim 1 comprising:

esterifying the carboxylic acid group of a hydroxy carboxylic acid with the hydroxy group of the same or a different hydroxy carboxylic acid, wherein the hydroxy carboxylic acid(s) contain from 2 to 8 carbon atoms to produce a carboxylic-acid terminated oligomer;

reacting the carboxylic-acid terminated oligomer with an olefinically-modified intermediate possessing one or more oxirane or oxetane groups and containing one or more terminal or pendant carbon-carbon double bonds and containing from 4 to 12 carbon atoms in the presence of catalyst to obtain olefinic functionalized oligomeric ester; and, hydrosilylating the olefinic-functionalized oligomeric ester with a hydride intermediate which is selected from the group of consisting of formulae (I-a)-(IV-a), (VI-a) and (VII-a)

$$AO_a R^4_b (B^H O_c R^{11}_d)_e C^H \quad \text{(I-a)}$$

$$AOC^H \quad \text{(II-a)}$$

$$AR^4 C^H \quad \text{(III-a)}$$

$$AR^4 B^H OC^H \quad \text{(IV-a)}$$

$$AOB^H OC^H \quad \text{(VI-a)}$$

$$AR^4 D^H \quad \text{(VII-a)}$$

wherein:
$A=R^1R^2R^3Si-$;
$B^H=-Si(R^5)(R^{6H})-$;
$C^H=R^7R^8R^{9H}Si-$; and,
$D^H=AR^{4H}$ subscripts a, b, c, d and e are each 0 or 1 and subject to the following provisos: a+b=1 and when e=1, c+d=1;

$R^1$, $R^2$, $R^3$, $R^5$, $R^7$, $R^8$ are each independently selected from the group consisting of monovalent hydrocarbon groups containing from 1 to 8 carbon atoms, monovalent aryl and alkaryl hydrocarbon groups containing from 6 to 12 carbon atoms, and $R^{10}$, wherein $R^{10}$ is selected from a group consisting of branched monovalent hydrocarbon groups of containing from 3 to 6 carbon atoms;

$R^4$ and $R^{11}$ are each independently selected from the group consisting of a divalent hydrocarbon group containing from 1 to 4 carbon atoms;

$R^{4H}$ is a linear or branched monovalent hydrocarbon radical of 1 to 12 carbon atoms;

$R^{6H}$ and $R^{9H}$ are each independently selected from the group consisting of linear or branched monovalent hydrocarbon groups containing from 1 to 8 carbon atoms, and hydrogen, provided that in formulae (I-a), (IV-a) and (VI-a), $R^{6H}$ and $R^{9H}$ are different and at least one $R^{6H}$ or $R^{9H}$ is hydrogen, to produce the ester-modified organosilicon having the formula (I).

16. An agricultural composition comprising (i) an agrochemical active ingredient; (ii) the polyalkylene-oxide free surfactant composition of claim 1; (iii) optionally one or more agrochemical excipients selected from the group consisting of buffers, preservatives and solvents; and, (iv) optionally one or more cosurfactants selected from the group consisting of nonionic, cationic, anionic, amphoteric, zwitterionic and polymeric surfactants.

17. The agricultural composition of claim 16 wherein the composition is one or more of an herbicide, a fungicide and an insecticide.

18. The agricultural composition of claim 17 wherein the agrochemical ingredient is glyphosate.

19. The agricultural composition of claim 16 applied to a crop or plant.

20. A coating application comprising the polyalkylene-oxide free surfactant composition of claim 1 wherein the coating application is selected from the group consisting of architecture coatings; OEM product coatings; industrial maintenance coatings; and, marine coatings.

21. A personal care composition comprising the polyalkylene-oxide free surfactant composition of claim 1.

22. A personal care composition which is an aqueous emulsion where the discontinuous phase comprises water and the continuous phase comprises the polyalkylene oxide free surfactant composition of claim 1.

23. A personal care composition which is an aqueous emulsion where the discontinuous phase comprises the polyalkyle-oxide free surfactant composition of claim 1 and the continuous phase comprises water.

24. A personal care composition which is a non-aqueous emulsion where the discontinuous phase comprises a non-aqueous hydroxylic solvent and the continuous phase comprises the polyalkylene-oxide free surfactant composition of claim 1.

25. A personal care composition which is a non-aqueous emulsion where the continuous phase comprises a non-aqueous hydroxylic organic solvent and the discontinuous phase comprises the polyalkylene-oxide free surfactant composition of claim 1.

26. A personal care application comprising the personal care composition of claim 21 wherein the personal care application is selected from the group consisting of deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, insect repellent and anti-aging products, color cosmetics such as lipsticks, foundations, face powders, eye liners, eye shadows, blushes, makeup, mascaras, and drug delivery systems for topical application of medicinal compositions that are to be applied to the skin.

27. The personal care application of claim 26 comprising at least one personal care ingredient selected from the group consisting of emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, volatile silicones, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

28. A home care composition comprising the polyalkylene-oxide free surfactant composition of claim 1.

29. A home care application comprising the home care composition of claim 28, wherein the home care application is selected from the group consisting of laundry detergent and fabric softener, dishwashing liquids, wood and furniture polish, floor polish, tub and tile cleaners, toilet bowl cleaners, hard surface cleaners, window cleaners, antifog agents, drain cleaners, auto-dish washing detergents and sheeting agents, carpet cleaners, prewash spotters, rust cleaners and scale removers.

* * * * *